(12) United States Patent
Patel

(10) Patent No.: US 6,417,140 B1
(45) Date of Patent: Jul. 9, 2002

(54) HERBICIDE SUSPENSION CONCENTRATES

(75) Inventor: Chhotubhai Dahyabhai Patel, Lansdale, PA (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 09/688,278

(22) Filed: Oct. 13, 2000

Related U.S. Application Data

(60) Provisional application No. 60/161,522, filed on Oct. 26, 1999.

(51) Int. Cl.[7] .................. A01N 25/22; A01N 33/22; A01N 57/02
(52) U.S. Cl. .................. 504/127; 504/363
(58) Field of Search .............. 504/127, 118, 504/363

(56) References Cited

U.S. PATENT DOCUMENTS

| | | | |
|---|---|---|---|
| 4,075,002 A | 2/1978 | Drewe et al. ............ 71/92 |
| 5,152,823 A | 10/1992 | Albrecht et al. ......... 71/79 |
| 5,397,766 A * | 3/1995 | Dexter ................. 504/128 |
| 5,795,847 A | 8/1998 | Nielsen et al. ......... 504/206 |
| 6,074,987 A * | 6/2000 | Shafer et al. .......... 504/132 |
| 6,165,939 A * | 12/2000 | Agbaje et al. ......... 504/105 |
| 6,165,940 A | 12/2000 | Aven .................. 504/118 |
| 6,245,713 B1 * | 6/2001 | Brinker et al. ........ 504/206 |

FOREIGN PATENT DOCUMENTS

| | | |
|---|---|---|
| EP | 1023 832 A1 | 1/2000 |
| EP | 1060667 A2 | 6/2000 |
| WO | WO 00/18227 | 4/2000 |
| WO | WO 00/64256 | 11/2000 |
| WO | WO 00/64258 | 11/2000 |

* cited by examiner

Primary Examiner—S. Mark Clardy

(57) ABSTRACT

The present invention relates to suspension concentrates of herbicide blends wherein one herbicide in the blend has a high water solubility, greater than 70 percent by weight, and one herbicide in the blend has very low water solubility, less than 1 percent by weight, and wherein the blend comprises a mixture of thickeners and surfactants.

6 Claims, No Drawings

HERBICIDE SUSPENSION CONCENTRATES

CROSS REFERENCE TO RELATED PATENT APPLICATIONS

This is a non-provisional application of prior pending U.S. provisional application Ser. No. 60/161,522 filed Oct. 26, 1999.

The present invention relates to suspension concentrates of herbicide blends wherein one herbicide in the blend has a high water solubility and one herbicide in the blend has very low water solubility.

Herbicides typically have a limited spectrum of activity, that is, a limited number of weeds that the herbicide controls. As a result, in order to obtain control of a mixed spectrum of weeds, a number of different herbicides are typically applied. This may be accomplished by applying different herbicides in a series of applications or, more often, by applying a mixture of herbicides in one application. Such mixtures are prepared by mixing the individual herbicides in a spray tank immediately prior to application or by combining the individual herbicides into a single formulation which is subsequently diluted in the spray tank prior to application.

The problem with mixing herbicides with significantly different physical/chemical properties is that they often are incompatible with each other. Such incompatibility may result in separation of the herbicides into one or more layers, crystallization of one or both of the herbicides to form an insoluble or non-suspensible mass in either a spray tank or, in the case of a formulation, the container. This problem is particularly acute when the formulation is water based rather than solvent based and one of the herbicides has a high solubility in water and one has a low solubility in water. It is even more acute when the low water soluble material has a small particle size. Water based formulations are preferred over solvent based formulations due to their reduced adverse environmental impact because of their lower content of volatile organic compounds.

Microemulsions or emulsions in water may work at low herbicide concentrations (e.g. less than 2% for the low solubility herbicide) but at higher concentrations crystal growth often occurs in the formulation and/or upon dilution with water for spraying.

I have discovered a unique combination of components which, when combined with an herbicide with water solubility less than one percent by weight and an herbicide with water solubility greater than 50 percent by weight at room temperature (ca. 25° C.), produce a stable suspension concentrate herbicide formulation. The stable suspension concentrate is a composition comprising:
  a) a first herbicide;
  b) a second herbicide;
  c) a thickener comprising:
    i) fumed silica; and
    ii) gelling clay or polysaccharide gum;
  d) one or more surfactants; and
  e) water;
    wherein:
    1) the water solubility of the first herbicide is less than one percent, preferably less than 0.5 percent, more preferably less than 0.1 percent, most preferably less than 0.01 percent;
    2) the water solubility of the second herbicide is greater than 50 percent, preferably greater than 70 percent, more preferably greater than 80 percent;
    3) the particle size of the first herbicide is less than 25 microns ("$\mu$") in size, preferably less than 10$\mu$, more preferably less than 5$\mu$, most preferably from 1 to 2$\mu$;
    4) the viscosity of the composition is from 200 to 1500 centipoise; and
    5) the composition is water dilutable.

For purposes of this invention, all percentages expressed herein are percent by weight, unless otherwise specified.

This composition overcomes the separation problems often encountered when mixing an aqueous suspension of a material with low water solubility and small particle size with an aqueous solution of a material with high water solubility, particularly when the aqueous solution has a high electrolyte concentration. The composition of the invention is a stable suspension concentrate formulation comprised of particles of the first herbicide which are less than 25$\mu$. Since the efficacy of pesticides is often related to the size of the pesticide particle, small particle size ensures that the biological activity of the first herbicide approaches that of a solvent-based emulsifiable concentrate of the herbicide. For this reason, there is a need to prepare pesticide formulations in which the pesticide has a small particle size. When water is used as the solvent there is an added benefit of eliminating organic solvents. Small particle size also ensures high suspensibility of the solid in the solution concentrate, typically greater than 90%. For purposes of this invention, particle size is calculated as the volume average particle size, determined either optically, with a scanning electron microscope, or using a commercial particle sizer, such as a Coulter LS™ particle sizer (Coulter Instruments).

The small particle size first herbicide may be prepared by milling larger particles using any one or more conventional milling techniques such as, for example, air milling, hammer milling, crushing (jaw, gyratory cone, roller, impact), impact milling (stationary plates), tumble milling with grinding media (balls, rods), roller milling (feeding through a small gap), pin milling, jet air milling (spiral, opposed, fluidized). For herbicides which melt at temperatures between 50° C. and 120° C. and are crystalline such as, for example, oxyfluorfen, a continuous melt emulsification-crystallization method is preferred. Preferably, the first herbicide is oxyfluorfen, fluoroglycofen ethyl, diuron, simizine, or azafenidin Most preferably, the first herbicide is oxyfluorfen. The first herbicide preferably comprises from 0.1 to 50 percent of the composition; more preferably 1 to 25 percent, even more preferably 1 to 5 percent, most preferably 1 to 3 percent.

The second herbicide has high water solubility. Preferably, the second herbicide is a water soluble salt such as, for example, salts of dicamba, acifluorfen, 2,4-dichlorophenoxyacetic acid, dalapon, dichlorprop-P, mecoprop, glufosinate, glyphosate, MCPB, fenoprop (silvex), trichloroacetic acid, sulfosate, or salts such as paraquat. Preferably the salt is a sodium, potassium, amino, monoalkylamino, or dialkylamino salt. For purposes of this invention "alkyl" means $C_1$–$C_4$ straight or branched chain alkyl. More preferably the salt is a sodium or alkylamino salt. Preferably the second herbicide is a salt of glyphosate or glufosinate. Most preferably, the second herbicide is the isopropylamine salt of glyphosate. Preferably, the second herbicide comprises from 0.1 to 70 percent of the composition; more preferably from 5 to 60 percent; even more preferably from 25 to 60 percent; most preferably from 40 to 60 percent.

I have discovered that in order to ensure that the first herbicide does not separate from the suspension concentrate a thickener comprising the combination of fumed silica (amorphous silicon dioxide) and a gelling agent selected from gelling clay or a polysaccharide gum is required. Preferred gelling agents are bentonite clays. Preferably the fumed silica comprises from 0.1 to 3.5 percent of the composition; more preferably 0.5 to 2 percent; most preferably 0.8 to 1 percent. Preferably the gelling agent comprises from 0.1 to 3.5 percent of the composition; more preferably 0.5 to 2 percent; most preferably 0.8 to 1 percent. The ratio of fumed silica to gelling agent is from 1:12.5 to 12.5:1 by weight; preferably 1:5 to 5:1; more preferably 2:1 to 1:2; most preferably approximately 1:1. Since the first herbicide comprises small particles it may also act as a thickener. For this reason, as the amount of first herbicide in the composition increases, the amount of thickener may be decreased. The appropriate ratio of first herbicide to thickener in the composition is adjusted such that the viscosity of the composition is from 150 to 1500 centipoise at room temperature (approximately 25° C.) measured using a standard viscometer such as, for example, a Brookfield viscometer with a #2 or #3 spindle at 30 rpm. Preferably the viscosity of the composition is from 150 to 1000 centipoise; more preferably from 300 to 400 centipoise.

In addition to the thickener, the composition must contain a surfactant. The surfactant acts as a wetting agent to enhance the compatibility of the first herbicide with the second herbicide and the thickener. Preferably the surfactant is an ionic surfactant; more preferably a salt of an alkyl aryl sulfonate; even more preferably a salt of dodecylbenzene-sulfonate; most preferably sodium dodecylbenzene-sulfonate. The surfactant comprises from 0.2 to 5 percent of the composition; preferably from 0.5 to 3 percent; more preferably from 1 to 2 percent.

Optionally, additional adjuvants may be incorporated into the composition including, for example, additional wetting agents (e. g., surfactants), spreading agents, dispersing agents, stickers, adhesives, processing aids (e. g., antifoaming agents), antifreeze agents (e. g., glycols such as ethylene, propylene, and dipropylene glycol), buffers, and stabilizers (e. g., inorganic salts). Such adjuvants commonly used in the art can be found in McCutcheon's Emulsifiers and Detergents, McCutcheon's Emulsifiers and Detergents/Functional Materials and McCutcheon's Functional Materials all published annually by McCutcheon Division of MC Publishing Company (New Jersey, USA) or *Detergents and Emulsifiers, Annual,* (Allured Publishing Company, Ridgewood, N.J., USA). When present, antifreeze agents may comprise up to 15 percent of the composition; preferably from 2 to 10 percent; more preferably 4 to 5 percent. When present, processing aids may comprise up to 2 percent of the composition; preferably from 0.1 to 1 percent, more preferably 0.1 to 0.2 percent. When present, stabilizers may comprise up to 3 percent of the composition; preferably 0.1 to 2 percent.

One advantage of the compositions of this invention is that not only are they stable themselves, but when diluted with water, for example, in a spray tank, they form a stable aqueous mixture. This is important because many herbicide mixtures are not stable when diluted with water. Instead, they form gels, insoluble solids, sticky masses, and/or foams which make it impossible to apply the diluted mixture to the weeds because of clogging of the spraying apparatus.

The compositions of this invention are useful for both preemergence and postemergence herbicides used to control monocot and/or dicot weeds depending upon the efficacy and selectivity of the first and second herbicides. Preemergence herbicides are usually applied to the soil either before, during or after seeding, but before the crop emerges. Postemergence herbicides are applied after the plants have emerged and during their growth period. The quantities of first and second herbicides required and the amount of the composition required for control of a particular spectrum of weeds will depend upon the growth stage of the weeds, the crop to be treated, and the relative potencies of the first and second herbicides. Under some conditions the compositions of the invention may be incorporated into the soil or other growth media prior to planting a crop. This incorporation may be by any convenient means, including mixing with the soil, applying the compositions to the surface of the soil and then discing or dragging into the soil to the desired depth, or by employing a liquid carrier.

It is often desirable, particularly in the case of foliar spray applications, to include in the spray tank one or more spray adjuvants not already incorporated into the formulation, such as, for example, wetting agents, spreading agents, dispersing agents, stickers, adhesives, and emulsifying agents in accordance with agricultural practices. Such adjuvants commonly used in the art are found in the John W. McCutcheon, Inc. publications described earlier.

For some applications, one or more additional herbicides may be added to the compositions of the present invention, thereby providing additional advantages and effectiveness. When additional herbicides are employed, the relative proportion used will depend upon the relative efficacy and selectivity of the first and second herbicides in the composition as well as the relative efficacy and selectivity of the additional herbicide or herbicides.

To prepare the composition, the components need not be combined in any particular order. However, to prevent unwanted separation of components and for ease of preparation, the following general sequence is preferred:

1) Prepare a suspension concentrate or slurry of the first herbicide in water;
2) Prepare a solution of the second herbicide in water;
3) Determine the amount of first herbicide suspension or slurry and the amount of second herbicide solution needed to provide the desired concentration of each in the final composition and the amount of water that each contain;
4) Determine the amount of each of the remaining components needed in the final composition;
5) Take the amount of water needed in the final composition (less the amount determined in step 3 above) and add to it the surfactant and water soluble optional components (e. g., antifreeze and processing aids), and mix until uniform;
6) Add the thickener, as individual components or a premix, and any water insoluble optional components, and mix until a uniform paste or slurry is formed;
7) Add the first herbicide suspension or slurry, and again mix until a uniform paste or slurry is formed; and
8) Add the second herbicide solution, and mix until the uniform suspension concentrate is formed.

One skilled in the art will recognize that any one of a variety of apparatus may be used to accomplish the mixing steps including; for example, colloid mills, sand mills, rotor/stator homogenizers, in-line emulsifiers, static mixers, piston homogenizers, ultrasonic homogenizers, and high-speed jets or nozzles. Preferred are colloid mills, rotor/stator mixers such as those available from Tekmar or Arde Burinco Companies, or a mixer such as a Cowles® dissolver.

The herbicide solution concentrate compositions of this invention can be diluted or applied as is to plant foliage and/or soil as aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the herbicide application rate, and the weeds to be controlled. The compositions can be mixed with fertilizers or fertilizing materials before their application. The compositions can be utilized as the sole pesticidal agent or they can be employed in conjunction with other pesticidal agents such as, for example, microbicides, fungicides, other herbicides, insecticides, and acaricides.

The following examples illustrate several aspects of this invention:

EXAMPLE 1

Preparation of an Oxyfluorfen/Glyphosate Suspension Concentrate

Using the general procedure outlined above, a suspension concentrate was prepared as follows (all parts are express as parts by weight):

1) Water (19 parts), antifreeze (propylene glycol, 5 parts), and processing aid (Antifoam™ C, Dow Chemical Co., 0.1 parts) are combined and mixed until uniform;

2) Surfactant (sodium dodecylbenzenesulfonate (Nacconol™ 90G surfactant, Stepan Co.), 1.0 parts) is added and the mixture mixed until uniform;

3) Thickener (1:1 mixture of fumed silica (Cab-O-Silm™ M-5 silica, Cabot Co.) and gelling clay (Min U Gel™ 400 clay, Floridin Co.), 1.4 parts) is mixed in until a uniform paste forms;

4) Oxyfluorfen suspension concentrate (6.5 parts) prepared as follows:

Eighty grams of oxyfluorfen herbicide (72% technical, melting point 75° C.) was melted with 6.4 g (8%, by weight, based on oxyfluorfen) of Sponto™ 234T surfactant (Witco Chemical Co.) in a 250 ml round bottom flask. The temperature was maintained at 105° C. The oxyfluorfen melt was pumped through heat-traced tubing and merged with a stream of water at 25° C. immediately before entering an in-line homogenizer (IKA Ultra Turrax TM homogenizer with a fine homogenizer tip) operating at 24,000 rpm. The flow rate of the oxyfluorfen stream was 15 ml/min. and the flow rate of the aqueous stream was 40 ml/min. The resulting suspension exiting the homogenizer was 28 percent solids. This suspension was concentrated to 41.7 percent oxyfluorfen; is mixed into the paste and the resulting mixture is again mixed until a second uniform paste results; and 5) Glyphosate isopropylamine salt solution (62 percent glyphosate isopropylamine, Monsanto Co., 67 parts) is added and the resulting mixture is mixed in a homogenizer until the final uniform suspension concentrate forms.

This suspension concentrate remained stable upon standing at room temperature. A comparable composition was prepared without the thickener mixture. Upon standing the comparable composition rapidly separated into two phases; a clear liquid phase containing the glyphosate isopropylamine salt and an aqueous suspension phase containing the oxyfluorfen. Similar results were obtained with comparable compositions which contained only one of the two thickener components.

EXAMPLE 2

Preparation of an Oxyfluorfen/Glyphosate Suspension Concentrate

Using the same general procedure as in Example 1, a second suspension concentrate was prepared with the following ratio of components:

| Component | Parts by Weight |
| --- | --- |
| Water | 11.8 |
| Antifreeze (propylene glycol) | 2.0 |
| Processing aid (Antifoam ™ C, Dow Chemical Co.) | 0.1 |
| Surfactant (sodium dodecylbenzene-sulfonate (Nacconol ™ 90G surfactant, Stepan Co.)) | 2.0 |
| Thickener (1:2 mixture of fumed silica (Cab-O-Sil ™ M-5 silica, Cabot Co.) and gelling clay (Min U Gel ™ 400 clay, Floridin Co.)) | 0.6 |
| Oxyfluorfen suspension concentrate (41.7 percent oxyfluorfen, Rohm and Haas Co.)) | 50.0 |
| Glyphosate isopropylamine salt solution (62 percent glyphosate isopropylamine, Monsanto Co.) | 33.5 |

This suspension concentrate remained stable upon standing at room temperature. When compared with comparable compositions without the thickeners, results were similar to those found with Example 1.

Biological Test Methods

Weed seeds and crop seeds were planted in a conventionally tilled field using a double disk planter in rows 18 centimeters apart. Treatments were applied postemergence after plants emerged to a height of approximately 3 to 12 centimeters. All treatments were applied with a bicycle sprayer equipped with 5 8002LP nozzles spaced 51 cm apart at a ground speed of 6.4 kilometers per hour to give a spray volume of 280 liters per hectare. The test was laid out in a completely randomized plot design with 4 replications. Individual plot dimensions were 2.5 by 6 meters. Formulated premixes and tank mixtures were diluted with water in a 2 liter bottle and sprayed using pressurized $CO_2$ as a propellant. All plots were rated for percent control at 7 and 33 days after treatment using a 0–100 scale with 0=no control and 100=all plants dead.

| Material | App. Rate g. ai. Ha | % Control[1] | | | | % Injury[2] | | |
| --- | --- | --- | --- | --- | --- | --- | --- | --- |
| | | Set fa | Cyp es | Brs ju | Ipo he | Trz ss | Glx ma | Sor vu |
| Ex. 1 | 280[3] | 95 | 79 | 99 | 89 | 85 | 78 | 73 |
| Ex. 1 | 1120[3] | 100 | 91 | 100 | 99 | 100 | 86 | 96 |
| oxy + gly[4] | 22 + 258 | 95 | 80 | 100 | 93 | 91 | 86 | 71 |
| oxy + gly[4] | 86 + 1034 | 100 | 93 | 100 | 100 | 100 | 92 | 95 |

[1]Percent control compared to untreated weeds
Weed abbreviations: Set fa = *Setaria faberi*, giant foxtail; Cyp es = *Cyperus esculentus*, yellow nutsedge; Brs ju = *Brassica juncea*, Indian mustard; Ipo he = *Ipomoea hederacea*, ivyleaf morningglory
[2]Percent control compared to untreated crops
Crop abbreviations: Trz ss = Triticum species, spring wheat; Glx ma = *Glycine max*, soybean; Sor vu = *Sorghum vulgare*, sorghum
[3]Calculated as the sum of oxyfluorfen and glyphosate (acid equivalent)
[4]oxyfluorfen mixed with isopropylamine salt of glyphosate (calculated as acid equivalent) in a spray tank These data indicate that there is no significant difference between the biological activity of the composition of this invention and the biological activity of the same materials when tank mixed.

I claim:

1. An herbicide composition comprising:
   a) 1 to 25 weight percent of oxyfluorfen;
   b) 5 to 60 weight percent of a salt of glyphosate;
   c) a thickener comprising:
      i) fumed silica; and
      ii) gelling clay or polysaccharide gum;
   d) one or more surfactants; and
   e) water;
   wherein:
      1) the particle size of the oxyfluorfen is less than 25 microns;

2) the viscosity of the composition is from 150 to 1500 centipoise; and
3) the composition is water dilutable.

2. The herbicide composition of claim 1 further comprising a third herbicide.

3. The herbicide composition of claim 1, wherein the gelling clay is a bentonite clay.

4. The herbicide composition of claim 1, wherein the surfactant is a salt of an alkyl aryl sulfonate.

5. The herbicide composition of claim 1, wherein the thickener comprises from 0.1 to 3.5 percent, by weight, of fumed silica and from 0.1 to 3.5 percent, by weight, of gelling clay or polysaccharide gum.

6. The herbicide composition of claim 1 further comprising an antifreeze agent and a processing aid.

* * * * *